(12) United States Patent
Forstner et al.

(10) Patent No.: US 6,447,457 B1
(45) Date of Patent: Sep. 10, 2002

(54) NON INVASIVE BLOOD PRESSURE MONITOR AND A METHOD FOR THE NON-INVASIVE MEASUREMENT OF THE BLOOD PRESSURE

(75) Inventors: Klaus Forstner, Asperg (DE); Gerhard Frick, Feldkirch (AT); Chung-Yueh Yen, Taichun (TW)

(73) Assignee: Microlife Intellectual Property GmbH, Berneck (CH)

( * ) Notice: Subject to any disclaimer, the term of this patent is extended or adjusted under 35 U.S.C. 154(b) by 17 days.

(21) Appl. No.: 09/710,897

(22) Filed: Nov. 14, 2000

Related U.S. Application Data
(60) Provisional application No. 60/165,664, filed on Nov. 16, 1999.

(51) Int. Cl.⁷ .................................................. A61B 5/02
(52) U.S. Cl. ...................................... 600/485; 600/496
(58) Field of Search ................................ 600/485, 490, 600/491, 473, 494, 495, 496, 499, 500, 502, 503

(56) References Cited

U.S. PATENT DOCUMENTS

| | | | |
|---|---|---|---|
| 4,517,986 A | * | 5/1985 | Bilgutay ..................... 600/490 |
| 4,667,680 A | | 5/1987 | Ellis |
| 4,747,412 A | * | 5/1988 | Yamaguchi ................. 600/490 |
| 4,850,368 A | * | 7/1989 | Miyawaki ................... 600/490 |
| 5,014,714 A | * | 5/1991 | Millay et al. ................ 600/490 |
| 5,590,661 A | * | 1/1997 | Ohmari et al. .............. 600/485 |
| 5,649,536 A | | 7/1997 | Ogura et al. |
| 5,752,919 A | | 5/1998 | Schrimpf |
| 6,045,510 A | * | 4/2000 | Ogura et al. ................ 600/485 |

FOREIGN PATENT DOCUMENTS

| | | |
|---|---|---|
| EP | 0 342 249 | 11/1989 |
| EP | 0 536 782 | 4/1993 |

* cited by examiner

Primary Examiner—Kevin Shaver
Assistant Examiner—Navin Natnitbithadha
(74) Attorney, Agent, or Firm—Shoemaker and Mattare

(57) ABSTRACT

A blood pressure measuring device is operatable in a first operating mode (M1) and in a second operating mode (M2). In the first operating mode, blood pressure values are based on one single measurement. In a second operating mode (M2), a mean value ($S_A$, $D_A$) of the systolic and the diastolic blood pressure is calculated on the basis of subsequent measurement values. The blood pressure monitor (1) is provided with means (2) for switching between the first operating mode (M1) and the second operating mode (M2).

7 Claims, 4 Drawing Sheets

NON INVASIVE BLOOD PRESSURE MONITOR AND A METHOD FOR THE NON-INVASIVE MEASUREMENT OF THE BLOOD PRESSURE

This application claims benefit of the filing date of provisional patent application No. 60/165,664, filed Nov. 16, 1999.

BACKGROUND OF THE INVENTION

The invention relates to an automatic, non-invasive blood pressure monitor and to a method for non-invasively measuring blood pressure with such a monitor.

Automatic electronic blood pressure monitors are known. These monitors determine the values of the systolic and the diastolic blood pressure e.g. on the basis of an oscillometric measurement. Other measurements are also known which may be based on electronic detection of Korotkoff sounds.

Automatic, electronic blood pressure measuring devices are usually applied on the upper arm of a patient, around the wrist or on a finger of the patient. While the measurement as such has proven to be sufficiently accurate with such devices, errors may occur due to the fact that a user is making movements during the measurement. Ideally, the blood pressure should be taken when the user is sitting down and has been at rest for some time.

It is a disadvantage of known blood pressure measuring devices, that wrong measurement values may be given if the device is not properly used, especially if the user did not rest sufficiently before the measurement. This is mainly the case with blood pressure monitors for the home use, such as oscillometric automatic blood pressure monitors.

SUMMARY OF THE INVENTION

It is an object of the present invention to overcome the drawbacks of the prior art, and in particular to provide an automatic, non-invasive blood pressure monitor suited for home use which allows reduction of measurement errors which are based on the fact that a user is moving during the measurement or does not rest sufficiently before the measurement. A further object of the invention is to provide a method for measuring the blood pressure which allows reduction of such errors.

Still a further object of the invention is to provide a non-invasive blood pressure monitor and a method for measuring the blood pressure which also allow fast determination of the blood pressure, if desired.

According to the present invention, these objects are solved with an automatic, non-invasive blood pressure monitor and with a method as described below.

The blood pressure monitor according to the present invention is operable in a first operating mode and in a second operating mode. In the first operating mode, blood pressure values are determined on the basis of one single measurement in a conventional manner.

In the second operating mode, the blood pressure values are calculated on the basis of a series of measurements. The inventive device can be used in the first operating mode for a quick and rough blood pressure measurement. The second operating mode allows a much more precise measurement. During a certain period of time, measurements are repeated and the value of the systolic and the diastolic blood pressure is determined as an average of several measurements. The second operating mode is especially advantageous because the measurement series lasts for a certain amount of time.

While the first measurement may be still erroneous because of insufficient rest of the user, the following measurements will be more accurate because the user will normally sit or lie down during the measurements. The device therefore is suitable for home use.

In a preferred embodiment, the blood pressure monitor comprises means for switching between the first operating mode and the second operating mode. The user may at its discretion choose if a fast rough measurement or a slower and more accurate measurement shall be made.

The blood pressure monitor preferably comprises means for calculating or determining a statistical distribution of the measured values and means for forming an average of a number of measured blood pressure values.

The means for forming the average are preferably programmed in such a way that a weighted average may be calculated.

It must be noted that the first and the second operating mode are independent from each other. The blood pressure monitor could only be operated in the first operating mode or in the second operating mode if this should be desired by the user. "First" and "second" does not relate to time sequences or a specific order or preference of the operating modes and it does not exclude other operating modes.

According to the method of the present invention, in the second operating mode an average value of the diastolic and the systolic blood pressure values is calculated and displayed.

In the second operating mode, a pause is preferably made between subsequent measurements. The pause can be about 60 seconds. This pause is advantageous in that it allows the measurement site (e.g. the upper arm or the wrist) to relax between measurements and in that it leads to an additional rest of the user.

In a further preferred embodiment, a statistical distribution of the blood pressure values is determined. Depending on the distribution, different calculation modes for calculating the average may be used. If one or more of the measured values substantially differs from the other measured values, a weighted average may be calculated. If all measured values are within a pre-determinable range, a normal, arithmetic average will be calculated.

In addition, if one or more of the measured values substantially differ from the others, an additional measurement may be made.

The method according to the present invention is also adapted to calculate the pulse rate with high accuracy. As the measurement lasts for quite a long time, a precise mean value of the pulse rate pressure may be calculated.

BRIEF DESCRIPTION OF THE DRAWINGS

The invention will be more clearly understood with reference to the drawings, in which.

DESCRIPTION OF THE PREFERRED EMBODIMENT(S)

Figure 1:
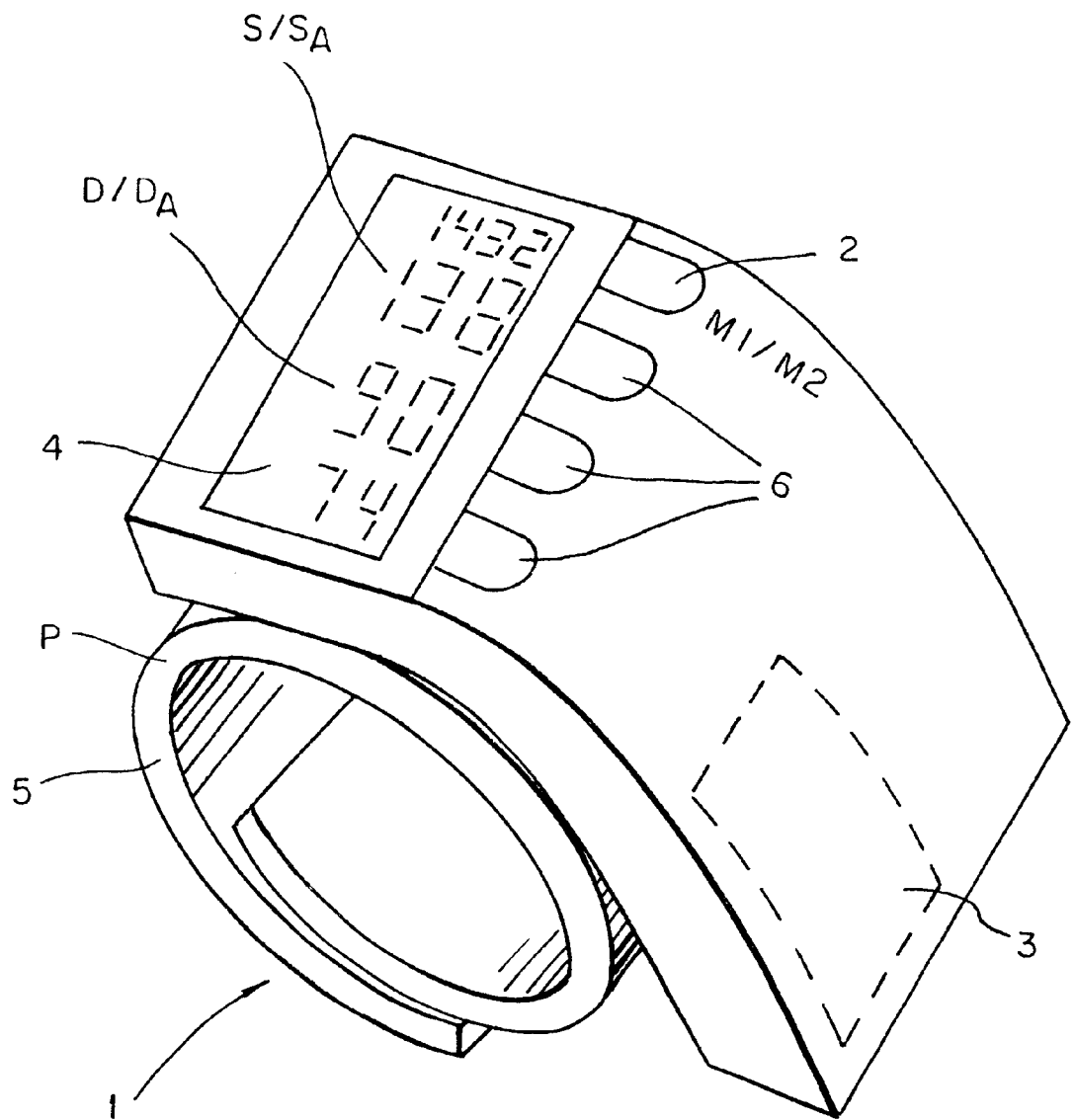
FIG. 1 is a perspective representation of a blood pressure measuring device according to the invention.

FIG. 1 shows a blood pressure measuring monitor 1. The blood pressure measuring monitor 1 includes a housing 10 and a cuff 5. The housing 10 comprises a digital display 4 for displaying measurement results such as the pulse rate, the systolic blood pressure or the diastolic blood pressure. The blood pressure monitor 1 further comprises a calculating arrangement 3 for calculating the blood pressure values and the pulse rate based on the pressure P within the cuff 5 with the oscillometric method. The pressure P may be measured in a conventional way with a pressure sensor (not shown).

Figure 2:
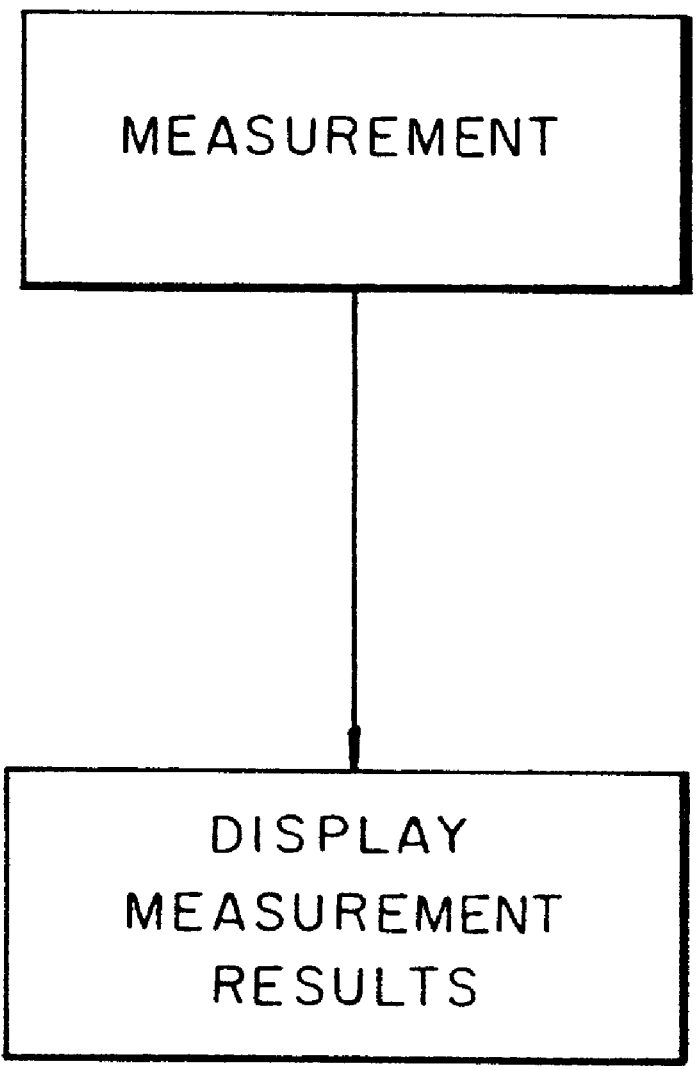
FIG. 2 is a flow chart of the first operating mode.
Figure 3:
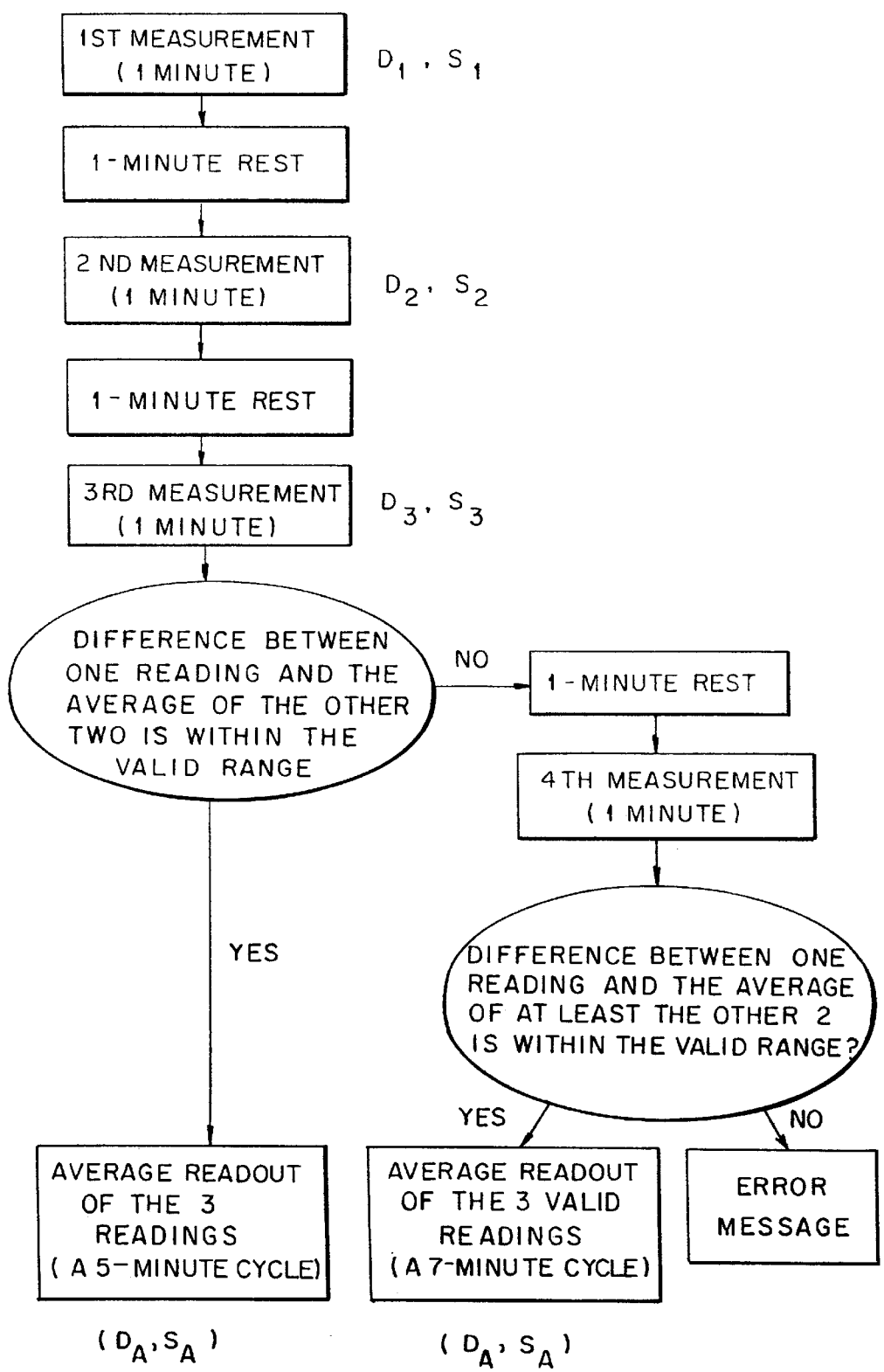
FIG. 3 is a flow chart of the second operating mode and FIG. 4 is a flow chart of the second operating mode of an alternative embodiment.

According to the invention, the blood pressure monitor is provided with a manual switch 2 for switching between a first operating mode M1 (see FIG. 2) and a second operating mode M2 (see FIG. 3). Additional buttons 6 are provided for resetting/turning on or off the device or starting the operation.

The blood pressure monitor 1 can be used either in the first operating mode M1 or in the second operating mode M2. In the first operating mode M1, the blood pressure measuring device is operating in a conventional manner. The value D of the diastolic blood pressure and the value S of the systolic blood pressure are measured in one single measurement cycle. This means that the cuff is inflated once and the pressure P within the cuff is measured during one deflation cycle.

In the second operating mode, a number of measurements is made. In each of these measurements, an actual value of the diastolic blood pressure D and of the systolic blood pressure S is determined and stored within the blood pressure monitor 1. After the last of the measurements, an average value $D_A$ of the diastolic blood pressures and an average value $S_A$ Of the systolic blood pressures is calculated in the calculating arrangement 3.

In FIG. 2, a schematic representation of a measurement in the first operating mode M1 is shown. One single measurement is taken. The measurement result is immediately displayed on the display 4.

In FIG. 3, a schematic representation of the second operating mode M2 is shown.

Three measurements are taken. Each measurement lasts for about 60 seconds. Between two subsequent measurement, a rest of another 60 seconds is made. This is necessary because between two measurements the venous re-flow has to be settled. This usually takes a minimum time of about 60 seconds. The time might be somewhat lower (50 seconds) or, of course, somewhat longer. The three measurements lead to three values D1, S1, D2, S2, D3, S3 of the systolic and the diastolic blood pressure, respectively.

After the third measurement, a comparison of the measured values is made. If all values are within a pre-determinable range, an average $D_A$, $S_A$ of the measured values is calculated.

The average of the diastolic blood pressure $D_A$ is formed as the arithmetic average of D1, D2 and D3. The average of the systolic blood pressure $S_A$ is formed as the arithmetic average S1, S2 and S3.

The valid range is about ±20 mm Hg for the systolic blood pressure and ±12 mm Hg for the diastolic blood pressure. This measurement cycle will take about 5 minutes.

If the measurement results of the three first measurements are not within the valid range, an additional measurement may be made. Usually, under physiological aspects, all measurement values shall be considered. Only in the case of errors due to motion artifacts or in case of an abnormal physiologic variation of the measurement results, one single result may be disregarded.

Usually, a variation of the measurement results during the three or four measurements does not necessarily lead to a rejection. People with unstable hemodynamic conditions often have systolic pressures which are outside the above mentioned pre-determinable range. Usually, these measurements are taken into consideration for calculating the average.

If the three first measurements are not within the valid range, in a first embodiment, an additional fourth measurement is made after a one minute rest. If the difference between one reading and the average of at least the other two is within the valid range, an arithmetic average of the three valid readings may be formed. This calculation leads to a seven-minute cycle. If no reading is within the valid range as compared to the average of the other two, an error message will be generated.

Usually, all artifact-free results need to be accepted. If three artifact-free results show a high variation (the difference between one reading and the average of the other two is outside the valid range), an additional average calculating mode may be applied (see FIG. 4).

If two consecutive values are within the valid range and a third value (e.g. the first or the last one) exceeds the valid range, the third value is compared with a weighted average. If the difference between the third value and the weighted average is still outside the valid range, the first two values will be accepted and a fourth measurement will be made.

If there are no two successive valid measurements, the values will be rejected. This applies when an excessive result is between two valid measurements.

The following examples will show how different measurement results will be treated. The examples are given for systolic pressures. Similar calculations apply for the diastolic pressure.

EXAMPLE 1

S1=100, S2=100, S3=161

In this case, two consecutive valid values are exceeded by one abnormal value (S3). In this case, the weighted average applies.

$$AW = \frac{(2 \cdot 100) + (2 \cdot 100) + 161)}{5} = 112$$

Since the difference between the third value and the weighted average is outside the valid range, a fourth measurement will be necessary in a similar way as shown in FIG. 3.

EXAMPLE 2

S1=100, S2=161, S3 100

As there are no consecutive similar values, a non weighed average shall be formed (average=120.33). The difference between all values and this average is outside the valid range. The whole measurement is not accepted because the patient's hemodynamic stability is not sufficient.

EXAMPLE 3

S1=161, S2=100, S3=100

This example is similar to example 1. The weighted average formula is applied. A fourth measurement is necessary.

EXAMPLE 4

S1=120, S2=150, S3=180

No consecutive values are found in this example. The normal average will be used. This patient does not have a hemodynamic stability necessary for a reasonable measurement. The average result will not be accepted and an error code will be displayed.

EXAMPLE 5

S1=120, S2=130, S4=140

All values are consecutive (which means there is no substantial difference between subsequent values). The normal non-weighted average is calculated. The average is 130. The difference between the average and all readings is within the valid range. An average value will be calculated and displayed.

Figure 4:
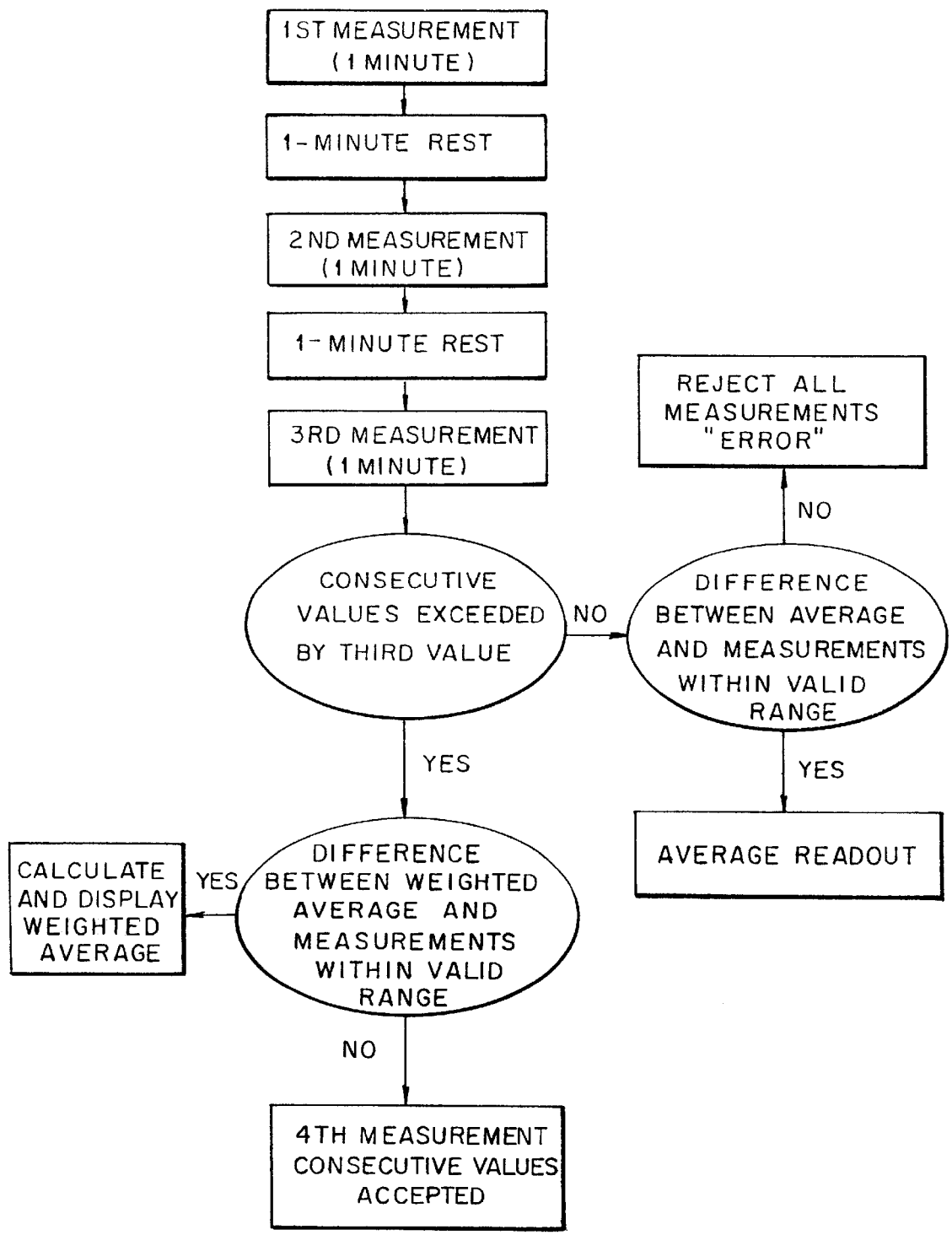

The sequence of the measurement is schematically shown in FIG. 4. As mentioned above, errors due to artifacts are rejected. Technical artifacts may be detected on the basis of pulse analysis. Physiologic rejections may be determined on the basis of statistic considerations.

The above algorithms show a possibility for a sophisticated calculation of an average value for the blood pressure values. This is basically possible with a blood pressure measuring device which is operable in the first operating mode M1 (which allows fast and rough measurement) and in the second operating mode M2 (which allows a precise average measurement).

What is claimed is:

1. An automatic, non-invasive blood pressure monitor for indicating the diastolic and systolic blood pressure of a patient, wherein:

the blood pressure monitor is operable in a first operating mode and in a second operating mode, in the first operating mode, said diastolic and systolic blood pressure values are determined on the basis of one single measurement, in the second operating mode, said diastolic and systolic blood pressure values are calculated as an average on the basis of a plurality of measured values of the diastolic and systolic blood pressure, and the blood pressure monitor comprises means for switching between the first operating mode and the second operating mode.

2. A blood pressure monitor according to claim 1, further comprising means for calculating a distribution of the values and means for forming a weighted average of the measured values.

3. A blood pressure monitor according to claim 1, wherein in the second operating mode, a pause of about sixty seconds is made between subsequent measurements.

4. A blood pressure monitor according to claim 1, further comprising means for forming a difference between the measured values and the average of the values and comparing the difference with a predetermined range.

5. A blood pressure monitor according to claim 4, further comprising means for forming a weighted average for comparison if one of the measured values substantially differs from the others.

6. A blood pressure monitor according to claim 5, further comprising means for making an additional measurement if the difference between the substantially differing measurement and the weighted average is outside a pre-determined range, and means for displaying a weighted average if the difference is within the predetermined range.

7. A blood pressure monitor according to claim 1, further comprising means for calculating a pulse rate.

* * * * *